United States Patent [19]

Hanes

[11] Patent Number: 4,642,392

[45] Date of Patent: Feb. 10, 1987

[54] CONJUGATED ALKADIENE TELOMERIZATION TO ORGANO-OXYALKADIENES

[75] Inventor: Ronnie M. Hanes, Milford, Ohio

[73] Assignee: National Distillers and Chemical Corporation, New York, N.Y.

[21] Appl. No.: 781,590

[22] Filed: Sep. 30, 1985

[51] Int. Cl.$^4$ ............................................. C07C 41/06
[52] U.S. Cl. .................................... 568/690; 568/657; 568/579; 568/669; 568/686
[58] Field of Search ............... 568/690, 657, 579, 689, 568/669, 686

[56] References Cited

U.S. PATENT DOCUMENTS 4,142,060  2/1979  Kuntz ................................. 568/657
4,196,135  4/1980  Enomoto et al. ................... 568/690

Primary Examiner—Howard T. Mars
Attorney, Agent, or Firm—Kenneth D. Tremain

[57] ABSTRACT

A process for the telomerization of a conjugated alkadiene with an alkanol is disclosed for the production of an organo-oxyalkadiene. A palladium catalyst having a phosphine or stibene ligand is employed in a substantially oxygen-free environment and in the presence of a high boiling solvent so that the reaction products may be separated from the catalyst by distillation. Vacuum fractional distillation is a preferred method for separating the products.

20 Claims, No Drawings

CONJUGATED ALKADIENE TELOMERIZATION TO ORGANO-OXYALKADIENES

TECHNICAL FIELD

The invention is directed to the telomerization of alkadienes with organic hydroxy compounds in the presence of a catalyst to produce an organo-oxyalkadiene.

PRIOR ART

The telomerization of conjugated alkadienes such as butadiene with alkanols in the presence of palladium-phosphine catalyst is a convenient route for the preparation of 8-methoxy-1,6-octadiene. Because of the high cost of palladium catalysts, any industrial process employing catalysts of this type requires recycling of the catalyst in order to minimize the cost of production. Accordingly, catalyst recovery and recycle is of primary concern along with selectivity, yields and speed of reaction in the selection of a catalyst for telomerization reactions of this type. Although palladium-phosphine type catalysts are effective for promoting these types of telomerization reactions after recovering and recycling the catalyst for subsequent reactions, it has been observed that the activity of the catalyst drops off significantly. Additionally, prior to recovering and recycling the catalyst the various products of the telomerization reaction must be separated by a process which does not substantially damage or deactivate the catalyst or cause a loss of the catalyst. The prior art method of recovering the telomerization product generally comprised distillation of the reaction products to remove them from the catalyst and resulted in catalyst loss and/or deactivation.

Accordingly, it is an object of the present invention to overcome these and other difficulties encountered in the prior art.

It is a further object of the present invention to provide a method for the telomerization of a conjugated alkadiene with an organic hydroxy compound to produce an organo-oxyalkadiene. It is a further object of the present invention to provide a process for conducting the aforesaid telomerization reaction by means of a palladium-type catalyst and which process provides a novel method for separating the organo-oxyalkadiene from the catalyst so that the catalyst can be recycled without substantial catalyst loss or substantial loss of catalyst activity.

SUMMARY OF THE INVENTION

These and other objects have been achieved according to the present invention which comprises a method for the telomerization of a conjugated alkadiene with an organic hydroxy compound to produce an organo-oxyalkadiene by reacting the aforesaid alkadiene and hydroxy compound in the presence of a palladium catalyst having a phosphine, arsine or stibene ligand. The process is conducted substantially in the absence of oxygen and in the presence of a solvent for the catalyst which has a boiling point substantially higher than that of the organo-oxyalkadiene so that the reaction products may be separated from the solution of the catalyst by distillation. The catalyst can thereafter be recycled for subsequent telomerization reactions.

It has been discovered that the ligand (e.g., phosphine, arsine or stibene ligand) in the catalyst was adversely affected by oxygen which resulted in substantial loss of catalyst activity up to the point where the catalyst was deactivated. By employing a high boiling solvent, the organo-oxyalkadiene can be distilled from the reaction mixture (which includes the catalyst) without having any substantial adverse affect on the catalyst. Vacuum fractional distillation is especially suitable for separating the organo-oxyalkadiene from the solution of catalyst without adversely affecting the catalyst although flash distillation and atmospheric distillation methods may be used.

DETAILED DESCRIPTION OF THE INVENTION

The present invention broadly relates to a method for the telomerization of a conjugated alkadiene with an organic-hydroxy compound to produce an organo-oxyalkadiene comprising reacting said alkadiene with said hydroxy compound with a catalytically effective amount of a catalyst compound comprising:

$$[PdR_1][YR_y^2]_2 \qquad (I)$$

$R^1$ is any anionic group displaced by methanol except the halides. $R^1$ especially comprises an organo acyclic or cyclic carboxylate group having from 1 to about 10 carbon atoms and especially a lower alkyl straight chain or branched chain carboxylate having from 1 to about 4 carbon atoms especially the acetate group. $R^2$ more particularly may comprise a straight chain, branched chain or cyclic radical having from 1 to about 10 carbon atoms and especially may comprise either a phenyl group or a lower alkyl group having from one to about 4 carbon atoms.

In the above formula (I) the moiety Y comprises either phosphorous, arsenic or antimony wherein y is the valence of Y.

In the above formula (I) ligands $[YR_y^2]$ may comprise:
Tributylphosphine
Tripentylphosphine
Trihexylphosphine
Tritolylphosphine
Triphenylphosphine
Tris(methoxyphenyl)phosphine
Triphenylphosphite
Tritolylphosphite
Trioctylphosphine
and the arsine and stibene homologs thereof.

The $R^2$ radical preferably comprises a phenyl group. The stibenes, arsines or phosphines containing alkyl groups are more susceptible to oxidation.

The palladium component of the catalyst complex herein can also be zero-valent palladium, a palladium-containing composition which will provide zerovalent palladium, i.e., will undergo reduction, under the conditions of the reaction and/or a palladium (II) salt, with or without the additional presence of a reducing agent such as alkali metal alkoxide, alkali metal acetate and/or alkali metal borohydride. Among such palladium-containing compositions are included palladium (II) acetate, palladium (II) formate, palladium (II) octanoate, palladium (II) propionate, palladium (II) nitrate, palladium (II) bis ($\pi$-allyl), palladium sulfate.

The telomerization reaction is conducted in the substantial absence of oxygen and especially under conditions in which oxygen is excluded to minimize the amount of catalyst ligand that must be replaced due to the oxidation of the stibene, arsine or phosphine moieties in the ligand. It has been discovered that the presence of even small quantities of oxygen has a deleterious affect in that oxygen causes ligand removal from the catalyst and the decomposition of the catalyst.

One of the catalysts employed according to the invention and falling within the scope of the above formula (I) is palladium acetate bis(triphenylphosphine) [Pd(OAc)$_2$][PPh$_3$]$_2$. This is one of the preferred catalysts.

In the above catalyst compound, [PdR$^1$] is referred to herein as the palladium component of the catalyst and [YR$_y^2$] as the ligand. When the catalyst is employed in the reaction of the present invention, the palladium and ligand dissociate so that under reaction conditions the ratio of palladium to ligand varies. Accordingly, by the addition of ligand or palladium to the reaction mixture containing the catalyst or by the adjustment of the reaction conditions (e.g., exclusion of oxygen) the ratio of ligand to palladium of the catalyst compound in the reaction millieu is controlled to anywhere from about 10:1 to about 1:1 and preferably a ratio of from about 5:1 to about 2:1 on a molar basis.

In another aspect of the invention, it has been discovered that the molar ratio of the alkadiene to the organic hydroxy compound influences the yield and selectivity of the reaction and that an excess of the organic hydroxy compound is required to maximize such yields and selectivities. By an excess it is meant that the organic hydroxy compound is present in more than a stoichiometric amount (i.e., greater than one mole of organic hydroxy compound to two moles of conjugated alkadiene). The molar ratio of the aforesaid hydroxy compound to the aforesaid alkadiene is from about 0.6:1 to about 3:1 and preferably from 0.75:1 to about 2.5:1.

The organic hydroxy compound specifically may comprise a compound having from 1 to about 10 carbon atoms and may be a saturated or unsaturated straight chain, branched chain or cyclic compound having at least one hydroxy group. Organic hydroxy compounds in this respect may comprise methanol, ethanol, 1-propanol, 2-propanol, 2-butanol, phenol, hydroxycyclohexane, hydroxycyclopentane and the like.

The conjugated alkadiene has anywhere from 4 to about 6 carbon atoms and comprises either butadiene, isoprene, chloroprene, piperylene, 1,3-pentadiene and the like.

One of the essential features of the present invention is to employ a solvent for the catalyst in which the boiling point of the solvent is higher than that of the organo-oxyalkadiene product that is produced as a result of the telomerization reaction. Generally, any solvent may be employed that is inert to the reactants and which does not have an adverse affect on the reaction. Solvents falling into this category may have a normal boiling point up to about 300° C. and generally comprise those solvents having a normal boiling point at least 20° C. higher than the organo-oxyalkadiene that is produced up to about 300° C. Solvents especially suitable in this regard comprise tetraglyme (dimethyl ether of tetraethylene glycol); dimethyl phthalate; dibutyl phthalate; dioctyl phthalate; methyl oleate; diphenyl oxide; diethylene glycol; diethylene glycol mono-sec butyl ether acetate (butyl Carbitol acetate); diethylene glycol monobutyl ether (butyl ethyl Cellosolve); dioctyl azelate; methyl benzoate; butyrolactone; and NMP (N-methylpyrrolidone).

After the organo-oxyalkadiene is formed, it may be separated from the solution of the catalyst and the solvent by distillation, such as by vacuum fractional distillation, flash distillation or atmospheric distillation. The distillation method is dictated by the temperature at which the separation of product by distillation is to be conducted. These temperatures preferably are from about 80° C. to 110° C. and are selected so as to avoid any adverse affects on the catalyst. Vacuum fractional distillation is the preferred method of separating the organo-oxyalkadiene. Standard vacuum distillation apparatus and methods are employed. It has been found that by separating the organo-oxyalkadiene from the catalyst in this manner, that the catalyst is not adversely affected by the separation process and may be recycled for further use in the telomerization reaction of the present invention.

It has also been found that by substantially excluding oxygen from the telomerization reaction and by employing the aforesaid class of organic solvents for the catalyst that the catalyst can be separated by distillation and recycled to the telomerization reaction in excess of 15 times without any substantial loss of catalyst activity i.e., selectivity and yield of the organo oxyalkadiene. Furthermore, between about 50 thousand to about 60 thousand moles of the organo-oxyalkadiene may be produced for each mole of catalyst employed according to the method of the present invention.

One of the advantages of the present invention is that about 90% selectivity to methoxyoctadiene is obtained at butadiene conversions of up to about 80%. Selectivities of from about 85% to about 95% at conversions of butadiene up to about 100% can be obtained with the catalyst and the method of the present invention when the telomerization reaction is conducted at temperatures from about 60° C. to about 80° C. for a period of time from about 15 to about 30 minutes. It has also been found that conversions and selectivities obtained in the telomerization reaction are independent of pressure.

It has also been discovered that selectivity and yields of the telomerization reaction may be optimized at about 65° C. to about 75° C. at autogenous pressures up to 200 psig in an inert atmosphere such as an atmosphere comprising nitrogen, one of the rare gases selected from group VIII A of the Periodic Table of Elements and various mixtures thereof.

In one embodiment, it has been discovered that butadiene may be telomerized with a lower alkanol such as methanol in the presence of a palladium acetate triphenylphosphine catalyst where the ratio of the triphenylphosphine to palladium acetate is from about 3 to about 5. A high boiling solvent such as tetraglyme and the equivalents thereof are also employed and the reaction is run at a temperature of about 70° C. to obtain high yields, selectivities and conversions to methoxyoctadiene. High selectivities to 8-methoxy-1,6-octadiene have been obtained in this regard with smaller amounts of 3-methoxy-1,7-octadiene also being produced, the ratio of 8-methoxy-1,6-octadiene to 3-methoxy-1,7-octadiene being greater than 4:1 on a molar basis. Optimum ratios of butadiene to alkanol and especially methanol were obtained by adjusting the molar ratios of butadiene to alkanol (i.e., methanol) to about 1 to about 1.2. By employing the method of the present invention in which oxygen is excluded from the reaction and the high boiling solvent is used for the catalyst so that the methoxyoctadiene may be separated by vacuum distillation the catalyst may be successfully reused in excess of about 15 times and from about 50 thousand to about 60 thousand moles of methoxyoctadiene may be produced for one mole of the palladium catalyst.

It has been found that during the successive recycling of the catalyst by the method described herein that even with substantial exclusion of oxygen from the process that the ligand is diminished and that in subsequent recycles of the catalyst thus recovered, small amounts of the ligand are added to the catalyst to replenish that proportion of ligand that is lost. Anywhere from about 1% to 10% of the theoretical amount of ligand is added to each successive recycle of the catalyst in this respect when proper precautions are taken to exclude oxygen from the reaction.

The following examples are illustrative.

EXAMPLE 1

A two liter 316 stainless steel, stirred reactor was charged with 0.16 gm (0.72 mmole) Pd(OAc)$_2$, 150 ml (150.5 gm or 677 mmole) tetraglyme, 225 ml (178 gm or 5.565 mmole) methanol, 0.942 gm (3.59 mmole) triphenylphosphine (PPh$_3$), 5.06 gm (46.8 mmole) anisole, and was purged 3 times with nitrogen. Anisole is an internal standard for glc analysis. The reactor was charged with butadiene 265 gm (4900 mmole) and the reactor and its contents heated to 75° C. held for 30 minutes at this temperature and cooled overnight.

The contents of the reactor were then discharged under inert atmosphere and distilled by vacuum distillation at 25 mm Hg pressure and 1,392.0 mmoles of 8-methoxy-1,6-octadiene were obtained along with 375.6 mmoles of 3-methoxy-1,7-octadiene.

The bottoms from the distillation process contained the palladium acetate triphenylphosphine catalyst and were recycled for subsequent telomerization of butadiene and methanol in substantially the same way as described above with the exception that additional triphenylphosphine ligand was added after each recycle of the catalyst and telomerization reaction. The triphenylphosphine added was anywhere from about 0.4 mmole to about 1.2 mmole in 12 recycles depending upon the amount of ligand that was determined to have been lost and substantially the same results were obtained as set forth in the above paragraph.

When the catalyst was recycled in subsequent reactions, anisole was not added to the reactor.

EXAMPLE 2

The procedure of Example 1 was substantially repeated in seven different telomerization reactions to study the affect of the methanol to butadiene ratio on ether telomerization reaction. The results are shown in Table I.

TABLE I

| METHANOL:BUTADIENE RATIO[a] | | | |
|---|---|---|---|
| | Ethers[c] | Selectivity (%)[c] | |
| M:B Ratio[b] | (mmoles) | Ethers | Octatriene |
| 0.4 | 51 | 75% | 5% |
| 0.653 | 78 | 81 | 6 |
| 0.894 | 112 | 87 | 6 |
| 1.115 | 128 | 89 | 6.5 |
| 1.35 | 140 | 96 | 4 |
| 1.58 | 102 | 94 | 4 |

TABLE I-continued

| METHANOL:BUTADIENE RATIO[a] | | | |
|---|---|---|---|
| | Ethers[c] | Selectivity (%)[c] | |
| M:B Ratio[b] | (mmoles) | Ethers | Octatriene |
| 1.83 | 62 | 95 | 5 |

[a]0.287 mmol Pd(OAc)$_2$, 0.574 mmol PPh$_3$, 30 ml dimethylphthalate, 5 ml anisole, total volume = 165 ml, 60° C.
[b]Methanol:butadiene molar ratio (as charged to reactor). Total of 130 ml total volume of methanol and liquid butadiene.
[c]Based on 15 mins. -0 min. sample results.

The methanol:butadiene stoichiometry is 0.5 and it would therefore be expected that this would be the optimum ratio of these two components in order to obtain methoxyoctadiene. The data in this table, therefore indicate that the selectivity and ether yield are maximized at a methanol: butadiene molar ratio greater than 1:1 which is unexpected.

EXAMPLE 3

The telomerization of butadiene to methoxyoctadiene was also studied in a continuous-stirred tank reactor. The preformed complex, Pd(OAc)$_2$(PPh$_3$)$_2$, was used as catalyst in dimethyl phthalate-methanol solution. Runs were assumed to have achieved steady-state when two criteria were met: (1) ether production was constant over at least the final three space-times (chemical steady-state) and (2) the dimethyl phthalate pumped in and out of the reactor balanced (physical steady-state). All such runs met both criteria.

In initial studies on temperature effects, highest selectivity to methoxyoctadiene (86%) was obtained at 70° C.; conversion increased from 16% to 80% as temperature was increased from 60° C. to 80° C. (Table II). Since ether yields were equivalent at 70° C. and 80° C. (64%) further studies were conducted at 70° C.

At a ligand to palladium ratio of 2, catalyst decomposition to palladium metal was observed in the reactor and 54% conversion was obtained. At higher ratios the catalyst was stable but conversion decreased above a ratio of 5. Maximum selectivity and conversion were attained at a ratio of 3.

The affect of reactant steady-state concentration on reaction rate was also determined in the continuous reactor (Table III). Reaction rates were high in most cases with maximum rate observed at 4.0M butadiene and 3.14M methanol. Butadiene conversion varied from 40 to 55% and ether selectivity varied from 91 to 94% in these runs. These data indicate that as the rate increased, ether selectivity also increased.

TABLE II

| BUTADIENE TELOMERIZATION TEMPERATURE EFFECT AT STEADY STATE[1] | | | |
|---|---|---|---|
| | Temp., °C. | | |
| | 60 | 70 | 80 |
| Ether Selectivity (%)[2] | 74 | 86 | 79 |
| Product Yield (%)[2] | 16 | 74 | 80 |

[1]Space time = 15 mins., [Pd] = 1.9 × 10$^{-3}$ M, PPh$_3$: Pd = 3.
[2]Based on products detected by glc techniques.

TABLE III

BUTADIENE TELOMERIZATION REACTANT CONCENTRATION EFFECT ON RATE[(1)]

| Steady-State Concentration | | Observed Ethers Space Time |
|---|---|---|
| Butadiene M | Methanol (M) | Yield (lbs/ft$^3$/hr) |
| 1.60 | 6.42 | 29 |
| 1.90 | 6.45 | 20 |
| 2.35 | 3.92 | 54 |
| 2.40 | 5.60 | 56 |
| 2.49 | 6.43 | 32 |
| 2.67 | 7.90 | 41 |
| 2.93 | 2.38 | 42 |
| 3.54 | 5.63 | 54 |
| 4.00 | 3.14 | 66 |

(1)[Pd] = 1.9 × 10$^{-3}$ M, PPh$_3$/Pd = 3, 70° C., 15 min. space time, 150 ml volume.

EXAMPLE 4

The telomerization reaction was also run in a 450 ml plug-flow reactor consisting of 77 ft-5 inches of ¼ inch I.D. stainless steel tubing immersed in a 73° C. water-/ethylene glycol bath. To this reactor were fed three streams: a catalyst solution of 0.0063M Pd(OAc)$_2$(PPh$_3$)$_2$ and 0.0063M PPh$_3$ in methyl benzoate (containing 9.1 volume percent methanol), fed at an average of 3.4 ml/min; methanol, fed at an average of 2.3 ml/min; and butadiene, fed at an average of 5.6 ml/min. The reactor was maintained at 95 psig in order to maintain liquid phase in the reactor. Over an eleven hour period with an average residence time of reactants in the reactor of 40.1 minutes the average yield of 8-methoxy-1,6-octadiene was 57.4% (based on butadiene fed) and 2.5 moles 8-methoxy-1,6-octadiene/liter reactor/hour were obtained. Average selectivity to 8-methoxy-1,6-octadiene was 81.1% (based on butadiene converted). No catalyst decomposition was observed.

The telomers obtained according to the method of the invention may be carbonylated to form unsaturated esters by art known methods. The esters obtained may be hydrogenated and used as lubricants, plasticizers or functional fluids or may be hydrolyzed to form an acid having unsaturated groups. The acid obtained may be incorporated into polyesters manufactured from phthalic anhydride, glycols and maleic anhydride and which are subsequently cross-linked with styrene all of which is known in the art. The unsaturated acid obtained provides a site along the polyester chain for cross-linking with styrene or equivalent monomers.

Although the invention has been described by reference to certain embodiments, it is not intended that the novel method for the telomerization of conjugated alkadienes with an organic hydroxy compound to produce an organo-oxyalkadiene be limited thereby but that modifications thereof are intended to be included as falling within the scope and spirit of the foregoing disclosure and the following claims.

What is claimed is:

1. A method for the telomerization of a conjugated alkadiene comprising reacting a conjugated alkadiene with an organic hydroxy compound, said organic hydroxy compound being employed in an amount in excess of the stoichiometric amount required for the telomerization of said organic hydroxy compound with said conjugated alkadiene, said reaction occurring in the presence of a catalytically effective amount of a catalyst compound comprising $$[PdR^1][YR_y^2]_2$$

where $R^1$ is any anionic group displaced by methanol except a halide; $R^2$ is a straight chain, branched chain or cyclic radical having from 1 to about 10 carbon atoms; Y is phosphorus or antimony; y is the valence of Y, the ligand:Pd ratio is maintained at from about 10:1 to about 1:1 during the reaction, said reaction being conducted in the substantial absence of oxygen and in the presence of an inert high boiling organic solvent, the boiling point of said solvent being greater than the boiling point of said organo-oxyalkadiene; separating said organo-oxyalkadiene from said catalyst and recycling said catalyst for the further telomerization of said conjugated alkadiene with said organic hydroxy compound.

2. The method of claim 1 wherein said conjugated alkadiene has from 4 to about 6 carbon atoms.

3. The method of claim 1 where said conjugated alkadiene is selected from butadiene, isoprene, chloroprene, piperylene and 1,3-pentadiene.

4. The method of claim 1 wherein said ligand:Pd ratio is maintained at from about 5:1 to about 2:1.

5. The method of claim 1 where said organic hydroxy compound comprises an alkanol.

6. The method of claim 5 where said organic hydroxy compound comprises a lower alkanol.

7. The method of claim 5 where said organic hydroxy compound comprises methanol.

8. The method of claim 1 where $R^1$ comprises an organo carboxylate group.

9. The method of claim 8 where $R^1$ comprises a lower alkyl ester group and $R^2$ comprises an aliphatic or cyclic unsaturated group and the molar ratio of said organic hydroxy compound to said conjugated alkadiene is greater than about 1:1.

10. The method of claim 1 wherein said reaction is conducted at a temperature of from about 65° C. to about 75° C. at autogenous pressures up to about 200 psig in an inert atmosphere.

11. A method for the telomerization of a conjugated alkadiene comprising reacting an alkadiene selected from the group consisting of butadiene, isoprene, chloroprene, piperylene and 1,3-pentadiene with an alkanol to produce an organo-oxyalkadiene, said alkanol employed in an amount of excess of the stoichiometric amount required for the telomerization of said alkanol with said conjugated alkadiene said reaction occuring in the presence of a catalytically effective amount of a catalyst compound comprising $$[PdR^1][YR_y^2]_2$$

where $R^1$ comprises a lower alkyl ester group; $R^2$ comprises a phenyl group or a lower alkyl group; Y is phosphorus or antimony; y is the valence of Y; and the ligand:Pd ratio is maintained at from about 5:1 to about 2:1 during the reaction, said reaction conducted in the substantial absence of oxygen and in the presence of an inert high boiling organic solvent for said catalyst, the boiling point of said solvent being greater than the boiling point of said organo-oxyalkadiene, separating said organo-oxyalkadiene from said catalyst by distillation at less than atmospheric pressure and recycling said catalyst for the further telomerization of said conjugated alkadiene with said alkanol.

12. The method of claim 11 where said organic hydroxy compound comprises a lower alkanol.

13. The method of claim 11 wherein $R^1$ comprises an organo-carboxylate group.

14. The method of claim 13 where $R^1$ comprises a lower alkyl ester group and $R^2$ comprises an aliphatic or cyclic unsaturated group and the molar ratio of said organic hydroxy compound to said conjugated alkadiene is greater than about 1:1.

15. The method of claim 11 wherein said reaction is conducted at a temperature of from about 65° C. to about 75° C. at autogenous pressures up to about 200 psig in an inert atmosphere.

16. The method of claim 11 wherein said conjugated alkadiene comprises butadiene.

17. The method of claim 16 where said alkanol comprises methanol and said organo-oxyalkadiene comprises methoxyoctadiene.

18. The method of claim 17 where said solvent is selected from tetraglyme, dimethylphthalate and methyl benzoate.

19. The method of claim 13 where said catalyst comprises [Pd(OAc)$_2$][PPh$_3$]$_2$.

20. The method of claim 11 wherein said catalyst is palladium acetate bis(triphenylphosphine).

* * * * *